US011471529B2

(12) United States Patent
Chen et al.

(10) Patent No.: US 11,471,529 B2
(45) Date of Patent: Oct. 18, 2022

(54) IMMUNOPOTENTIATOR, FOOT-AND-MOUTH DISEASE INACTIVATED VACCINE AND PREPARATION METHOD THEREOF

(71) Applicant: JIANGSU ACADEMY OF AGRICULTURAL SCIENCES, Nanjing (CN)

(72) Inventors: Jin Chen, Nanjing (CN); Xiaoming Yu, Nanjing (CN); Qisheng Zheng, Nanjing (CN); Liting Hou, Nanjing (CN); Yiwei Wang, Nanjing (CN); Yuanpeng Zhang, Nanjing (CN); Xuwen Qiao, Nanjing (CN); Jibo Hou, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 39 days.

(21) Appl. No.: 17/034,934

(22) Filed: Sep. 28, 2020

(65) Prior Publication Data

US 2021/0015913 A1    Jan. 21, 2021

Related U.S. Application Data

(63) Continuation-in-part of application No. 16/063,209, filed on Jun. 15, 2018, now abandoned.

(51) Int. Cl.
*A61K 39/39* (2006.01)
*A61K 39/135* (2006.01)
*A61K 39/00* (2006.01)

(52) U.S. Cl.
CPC ............ *A61K 39/39* (2013.01); *A61K 39/135* (2013.01); *A61K 2039/5252* (2013.01); *A61K 2039/5555* (2013.01); *A61K 2039/55572* (2013.01); *A61K 2039/55583* (2013.01)

(58) Field of Classification Search
CPC .................. A61K 39/39; A61K 39/135; A61K 2039/5252; A61K 2039/5555; A61K 2039/55572; A61K 2039/55583; A61K 39/12; C12N 2770/32134
See application file for complete search history.

(56) References Cited

PUBLICATIONS

Li J, Zhong Y, Li H, Zhang N, Ma W, Cheng G, Liu F, Liu F, Xu J. Enhancement of Astragalus polysaccharide on the immune responses in pigs inoculated with foot-and-mouth disease virus vaccine. Int J Biol Macromol. Oct. 1, 2011;49(3):362-8. Epub May 27, 2011. (Year: 2011).*

* cited by examiner

*Primary Examiner* — Rachel B Gill
(74) *Attorney, Agent, or Firm* — CBM Patent Consulting, LLC (57) ABSTRACT

The present invention relates to the preparation of the compound immunopotentiator and the application thereof in a foot-and-mouth disease vaccine of pigs. According to the present invention, the foot-and-mouth disease vaccine of pigs is taken as a research subject, and on this basis, several immunopotentiators having obvious immunopotentiating effects are selected for the compound immunopotentiator, and an antigen/vaccine is mixed with the immunopotentiator to prepare a vaccine-immunized pig. An animal experiment result shows that the present invention has obvious immunopotentiating effects. After immunizing the vaccine containing the compound immunopotentiator, a window period for antibody production can be significantly shortened to 7 days; a LPB-ELISA antibody titer is significantly improved, and an antibody pass rate is significantly increased; an immune protection period is also significantly extended, at least up to 7 months.

8 Claims, 5 Drawing Sheets

IMMUNOPOTENTIATOR, FOOT-AND-MOUTH DISEASE INACTIVATED VACCINE AND PREPARATION METHOD THEREOF

This application is a continuation in part of U.S. patent application Ser. No. 16/063,209 filed 15 Jun. 2018 that is the U.S. national phase of International Application No. PCT/CN2017/094856 filed on 28 Jul. 2017 which designated the U.S. and claims priority to Chinese Application Nos. filed on CN201710441094X filed on 13 Jun. 2017, the entire contents of each of which are hereby incorporated by reference.

TECHNICAL FIELD

The present invention relates to the field of biopharmaceuticals, and more particularly, to an immunopotentiator, a foot-and-mouth disease inactivated vaccine, and a preparation method thereof.

BACKGROUND

Foot-and-mouth disease (FMD) is an acute, febrile, highly contagious infectious disease caused by a foot-and-mouth-disease virus (FMDV). The foot and mouth disease virus belongs to the Aphthovirus of Picornaviridae, and has seven serotypes: types A, O, C, SAT1, SAT2, SAT3, and Asia 1, and each serotype further contain several subtypes. The virus has no cross-immunity among various types, and only partial cross-immunity exists among the subtypes of the same serotype. In 2012, the General Office of the State Council issued National Medium and Long-Term Programme for Animal Disease Control (2012-2020), which classified the foot-and-mouth disease as one of the diseases that should be preferentially prevented and controlled.

In China, the foot-and-mouth disease vaccine belongs to a mandatory immune vaccine. An inactivated vaccine is a mainly used currently. However, the inactivated vaccine also has the deficiencies such as slow antibody production, short immunity period, narrow antigen spectrum, and incomplete inactivation. Now, many researchers are improving and researching new inactivated vaccines, such as new prevalent strains and production processes, making purer antigens, better immune effects, more effective adjuvants, and more reliable inactivation, but the research period and verification cycle for each process are relatively long. The frequency of conventional foot-and-mouth disease vaccine immunization for pigs is generally 2 to 3 times, but the duration of immune protection is only 3 to 4 months, and the maximum protective effect is only 70 to 80% after immunization strengthening. Therefore, there is a great space for improving the quality of foot-and-mouth disease vaccines, and one of the feasible technical approaches is improvement of the immunopotentiator.

*Astragalus mongholicus* (scientific name: *Astragalus mongholicus* Bunge) is *astragalus* in leguminosae, also known as *astragalus mongolicus* or *Astragalus membranaceus*, which is a perennial herb, with a height of 50 cm to 80 cm. The *astragalus mongholicus* has a deep and thick main root, and an erect stem which has multiple branches on an upper part and is villous. Singular pinnately compound leaves grow alternatively, with 12 pairs to 18 pairs of leaflets. Racemes are axillary, with 10 to 25 flowers loosely arranged; bracts are linear and lanceolate; and small pedicels are covered with black hirsute. Pods are membranous and swollen in an ovate oblong, with a length of 1.1 cm to 1.5 cm. There are 5 to 6 black seeds which are reniform. A flowering phase is June to July, and a fruit phase lasts for 8 months to 9 months. The *astragalus mongholicus* is distributed in Russia, North Korea, Mongolia and China; and is distributed in Heilongjiang (Hulunbeier League), Inner Mongolia, Hebei, Shanxi, Xinjiang, Jilin and other places in China, growing on sunny grasslands and slopes. Roots thereof are used medicinally for invigoration of qi for consolidating superficies, diuresis and detoxification, apocenosis, and healing up of sore and promotion of tissue regeneration. The *astragalus* mongholicus has good curative effects in protecting myocardium, regulating blood pressure and improving human immunity.

An *astragalus* polysaccharide is a water-soluble heteropolysaccharide obtained by extracting, concentrating and purifying dried roots of the *astragalus mongholicus* or the *Astragalus membranaceus* in leguminosae, and the *astragalus* polysaccharide can significantly enhance the non-specific immunity function and humoral immunity function. The *astragalus* polysaccharide can induce a body to produce interferon to interfere with virus replication in the body, and improve the immunity function of the body; and can strengthen and stimulate the formation of lymphocytes and reticuloendothelial cells, enhance phagocytic functions of the reticuloendothelial cells and macrophages, and have good promotion and regulation effects on humoral, mucosal and cellular immunity. As a feed additive applied in animal breeding, the *astragalus* polysaccharide has the effects of promoting animal growth and improving body immunity. As a natural product, the *astragalus* polysaccharide is rich in sources, low in price, has small cytotoxic side effects on histocytes when being used for a long term, and has low residues. However, the amount added in feed or drinking water is large, and the basic amount is at least g/day, resulting in greater waste; moreover, the immunopotentiating effects are inaccurate, or difficult to evaluate.

Toll-like receptors (TLRs) are a class of transmembrane proteins present in mammalian immunocytes, the main immunological functions of which are to monitor and identify various pathogenic microorganism-related molecules (TLR agonists), and rapidly induce innate immune responses, laying a foundation for antigen-specific acquired immune responses. Studis of applying the TLR agonists to veterinary vaccines are mostly in the laboratory. A large number of study results have shown that the TLR agonists can be used as vaccine immunopotentiators. Adding the TLR agonists to the vaccines, such as CpG, polyI:C, imiquimod, have significant immunopotentiating effects. The TLR4 agonist was approved for use in hepatitis B and human papilloma virus vaccines in 2009.

The main application bottleneck at present is that the manufacturing costs of most TLR agonists are too high.

SUMMARY

Object of the present invention: a technical problem to be solved by the present invention is to provide a compound immunopotentiator. The invention aims to provide a compound immunopotentiator, which can generate synergistic effects by using a trace amount of TLR agonist and using a trace amount of traditional Chinese medicine immunopotentiator *astragalus* polysaccharide, which not only reduces the cost of solely using a TLR agonist immunopotentiator, but also improves the immunity and preferably improves the immune effects of the foot-and-mouth disease vaccines, can protect piglets to slaughter by one injection, shorten the window period for antibody production to seven days, extend the antibody duration to more than seven months, and significantly reduce the cost of raising pigs.

Another technical problem to be solved by the present invention is to provide a preparation method of the compound immunopotentiator.

Another technical problem to be solved by the present invention is to provide a foot-and-mouth disease inactivated vaccine containing the compound immunopotentiator.

The last technical problem to be solved by the present invention is to provide a preparation method of the foot-and-mouth disease inactivated vaccine containing the compound immunopotentiator.

Technical solution: in order to solve the above problems, the technical solution of the present invention is to provide a compound immunopotentiator, which comprises, but is not limited to contain 5 to 520 μg/mL monophosphoryl lipid A, 10 to 520 μg/mL muramyl dipeptide, 1 to 520 μg/mL β-glucan, and 0.05 to 5.2 mg/mL *astragalus* polysaccharide.

Preferably, the above compound immunopotentiator comprises, but is not limited to contain 5 to 500 μg/mL monophosphoryl lipid, 10 to 500 μg/mL muramyl dipeptide, 1 to 500 μg/mL β-glucan, and 0.05 to 5.0 mg/mL *astragalus* polysaccharide.

Preferably, the above-mentioned compound immunopotentiator comprises, but is not limited to contain 100 to 500 μg/mL monophosphoryl lipid, 100 to 500 μg/mL muramyl dipeptide, 50 to 500 μg/mL β-glucan, and 1 to 5.0 mg/mL *astragalus* polysaccharide.

The present invention further comprises a preparation method of the above immunopotentiator, which comprises, but is not limited to the following steps:

1) preparing a solution containing monophosphoryl lipid A, muramyl dipeptide, β-glucan and *astragalus* polysaccharide, and mixing the solution with Tween-80 to obtain an aqueous phase;

2) mixing Marcol 52 mineral oil and Span-80 to obtain an oil solution; and 3) mixing and emulsifying the aqueous phase and the oil solution to obtain a partner vaccine containing a compound immunopotentiator.

The present invention further comprises an application of the above immunopotentiator in vaccine preparation.

The present invention further comprises a foot-and-mouth disease inactivated vaccine containing the compound immunopotentiator above.

The above foot-and-mouth disease inactivated vaccine further comprises, but is not limited to, an inactivated antigen solution.

A volume ratio of the inactivated antigen solution to the compound immunopotentiator in the foot-and-mouth disease inactivated vaccine is 9:1 to 8:1.

The above inactivated antigen solution is one or more of an O, A and Asia-I foot-and-mouth disease inactivated antigen, polypeptide or other genetically engineered expression product.

The present invention further comprises a preparation method of the above foot-and-mouth disease inactivated vaccine containing the compound immunopotentiator, which comprises, but is not limited to the following steps:

1) mixing the compound immunopotentiator with an inactivated antigen solution, and then thoroughly mixing the mixture with Tween-80 to obtain an aqueous phase);

2) mixing Marcol 52 mineral oil and Span-80 to obtain an oil phase; and 3) thoroughly mixing the aqueous phase with the oil solution, thus obtaining the foot-and-mouth disease inactivated vaccine containing a compound immunopotentiator.

Beneficial effects: compared with the prior art, the present invention has the following advantages.

1. The present invention develops a compound immunopotentiator, which can be used in combination with a foot-and-mouth disease inactivated vaccine to effectively improve the efficacy of the vaccine, not only can improve the antibody pass rate and average antibody level, but also can significantly shorten the window period for antibody production to seven days, and increase the antibody duration to more than seven months.

2. The *astragalus* polysaccharides is rich in sources, low in price, has small cytotoxic side effects on histocytes when being used for a long term, and has low residues. Adding a small amount of *astragalus* polysaccharides can significantly reduce the dosages of other three TOLL-like receptor agonists and reduce the production cost by 90(90%) without reducing the immune efficacy.

3. The combined use of the compound immunopotentiator and the foot-and-mouth disease inactivated vaccine of the present invention can significantly improve the immune effects of the vaccine. Pig farms can reduce the vaccine immunization times according to the situations thereof, thus reducing the cost of breeding and reducing the swinery stress.

DETAILED DESCRIPTION

The present invention is further explained with reference to the drawings hereinafter.

First Embodiment: Preparation of Compound Immunopotentiator and Foot-and-Mouth Disease Vaccine 1. Experimental Materials Monophosphoryl lipid A abbreviated as MPL.

Muramyl dipeptide abbreviated as MDP.

MPL, MDP and β-glucan were all purchased from InvivoGen.

*Astragalus* polysaccharide is prepared from *Astragalus membranaceus*.

ISA206 was purchased from SEPPIC; Marcol 52 mineral oil, Span, and Tween were purchased by the laboratory.

Inactivated porcine FMD O type virus solution (98 strains of porcine FMD O type virus in Myanmar) was inactivated by diethyleneimine, and the content was 5.8 μg/mL in 146s, which was a gift from THE SPIRIT JINYU BIOLOGICAL PHARMACEUTICAL CO., LTD.

Commercially available FMD O, A and Asia-I trivalent vaccine were purchased from THE SPIRIT JINYU BIOLOGICAL PHARMACEUTICAL CO., LTD.

6-7 weeks old healthy susceptible piglets, with liquid-phase blocking ELISA antibody titer no more than 1:8.

In the present invention, a LPB-ELISA antibody titer was detected using a foot-and-mouth disease ELISA kit (Lanzhou Veterinary Research Institute).

1. Configuration of Immunopotentiator

The main ingredients of the immunopotentiator are: monophosphoryl lipid A (MPL), muramyl dipeptide (MDP), β-glucan, and *astragalus* polysaccharide. It is prepared by dissolving each main ingredient in 0.1 M Tris-HCl with a pH of 8.0.

Compound immunopotentiator 1: The final concentrations of MPL, MDP, β-glucan and *astragalus* polysaccharide were configured to 5 μg/mL, 10 μg/mL, 1 μg/mL and 0.05 mg/mL respectively.

Compound immunopotentiator 2: the final concentrations of MPL, MDP, β-glucan and *astragalus* polysaccharide were configured to 100 μg/mL, 100 μg/mL, 50 μg/mL and 1 mg/mL respectively.

Compound immunopotentiator 3: the final concentrations of MPL, MDP, β-glucan and *astragalus* polysaccharide were configured to 500 μg/mL, 500 μg/mL, 500 μg/mL and 5 mg/mL respectively.

Compound immunopotentiator 4: the final concentrations of MPL, MDP, β-glucan, and *astragalus* polysaccharide were configured to 5 μg/mL, 10 μg/mL, 1 μg/mL and 20 mg/mL respectively.

Compound immunopotentiator 5: the final concentrations of MPL, MDP, β-glucan and *astragalus* polysaccharide were configured to 500 μg/mL, 500 μg/mL, 500 μg/mL and 20 mg/mL respectively.

Compound immunopotentiator 1-1: the final concentrations of MPL, MDP, β-glucan, and *astragalus* polysaccharide were configured to 5 μg/mL, 10 μg/mL and 1 μg/mL respectively.

Compound immunopotentiator 3-1: the final concentrations of MPL, MDP, β-glucan, and *astragalus* polysaccharide were configured to 500 μg/mL, 500 μg/mL and 500 μg/mL respectively.

Immunopotentiator 6: the final concentration of *astragalus* polysaccharide was configured to 20 mg/mL.

Immunopotentiator 7: the final concentration of *astragalus* polysaccharide was configured to 5 mg/mL.

Immunopotentiator 8: the final concentrations of MPL, MDP, and β-glucan were configured to 2 mg/mL, 40 mg/mL and 0.2 mg/mL, respectively.

The prepared compound immunopotentiator was filtered (0.22 μm filter) and sterilized, and then was p sub-packaged in green bottles and stored at 4° C.

Preparation of *Astragalus* Polysaccharide:

The *astragalus* polysaccharide is a powder made by extraction and processing from *Astragalus membranaceus.*

1) Soaking *Astragalus membranaceus* in an equal amount of distilled water by weight for 2 to 12 hours, boiling the mixture for one hour, collecting supernatant; 2) adding additional equal amount of distilled water to the precipitates for boiling the mixture for one hour collecting supernatant, and repeat step 2); 3) combining three supernatants, filter, and concentrate the filtrate under reduced pressure to contain about 1 g crude polysaccharide in 1 ml of supernatant; and 4) precipitating the crude polysaccharide with 60% and 80% ethanol filtering, adding distilled water to dissolve the precipitate, drying to yield the *astragalus* polysaccharide that is used for preparing the foot-and-mouth disease vaccine.

Preparation Method of Foot-and-Mouth Disease Vaccine

First method: preparing a compound immunopotentiator partner vaccine, that is, thoroughly mixing the compound immunopotentiator and Tween in a volume ratio of 96 to 4 as an aqueous phase; evenly mixing Marcol 52 mineral oil and Span in a volume ratio of 96 to 4 as an oil phase; and preparing a vaccine in a volume ratio of 1 to 2 (aqueous phase to oil phase), wherein the prepared vaccine was the compound immunopotentiator partner vaccine namely. The compound immunopotentiator partner vaccine should be sufficiently mixed with a commercially available vaccine at a volume ratio of 1 to 9 before use.

Second method: The compound immunopotentiator and the inactivated porcine O-type foot-and-mouth disease virus solution were mixed thoroughly in a volume ratio of 1 to 9 to prepare an aqueous phase. ISA206 and the aqueous phase were placed at room temperature for approximately 30 minutes firstly. The ISA206 was placed into an emulsification tank, and the aqueous phase was placed into the emulsification tank at 200 rpm/min, and then stirred evenly; and the mixture was stirred for 10 minutes at 2000 rpm/min to obtain a vaccine, wherein a volume ratio of the aqueous phase to the ISA206 was 46 to 54.

The vaccines prepared by the above two methods have basically the same immune effects under the same final concentration of the compound immunopotentiator, but are convenient for users with different requirements in production.

In this embodiment, the constituent of the compound immunopotentiator can be flexibly matched within given range, and are not listed one by one herein.

Second Embodiment: Evaluation of Immune Effects of Compound Immunopotentiator on Inactivated Foot-and-Mouth Disease Inactivated Vaccine 1. Preparation of Vaccine In the embodiment, a foot-and-mouth disease vaccine was prepared according to the second method of the first embodiment:

The compound immunopotentiator 1 and an inactivated antigen were mixed in a ratio of 1 to 9 as an aqueous phase, the ISA206 was placed in an emulsifying tank; at 200 rpm/min, the aqueous phase was placed in the emulsifying tank, and the mixture was stirred evenly; and then the mixture was stirred for 10 minutes at 2000 rpm/min, and the foot-and-mouth disease inactivated vaccine prepared was called FMD inactivated vaccine 1 containing compound immunopotentiator: and referred to as FMD.

The preparation methods of vaccines of the compound immunopotentiators 2, 3, 4, 5, 6, and 7 were the same as that of the compound immunopotentiator 1, and FMD inactivated vaccines 2, 3, 4, 5, 6, and 7 containing the compound immunopotentiators were prepared, and were referred to as FMD 2, 3, 4, 5, 6, and 7.

The immunopotentiator 8 was mixed with the inactivated antigen in a ratio of 1 to 1, the foot-and-mouth disease inactivated vaccine prepared was called FMD inactivated vaccine 8 containing compound immunopotentiator, and referred to as FMD 8 (the vaccine was prepared according to patent ZL201310042983.0, wherein the immunopotentiator and the inactivated porcine foot-and-mouth disease virus solution were mixed in a volume ratio of 1 to 1, so as to obtain an aqueous phase. The ISA206 and the aqueous phase were placed at room temperature for approximately 30 minutes respectively. The ISA206 was placed in an emulsifying tank; at 200 rpm/min, the aqueous phase was placed in the emulsifying tank and stirred evenly, and stirred for 10 minutes at 2000 rpm/min, to obtain a vaccine).

0.1M Tris-HCl with a pH of 8.0 and an inactivated antigen were mixed in a ratio of 1 to 9 as an aqueous phase, the ISA206 was placed in an emulsifying tank; at 200 rpm/min, the aqueous phase was placed in the emulsifying tank, and stirred evenly; and then the mixture was stirred for 10 minutes at 2000 rpm/min, and the foot-and-mouth disease inactivated vaccine prepared was called FMD control vaccine.

2. Grouping, Immunization and Antibody Detection

Experimental grouping and immunization: healthy susceptible piglets were randomly divided into six groups in total with each group having 10 piglets. Each group of vaccines was immunized with one group of healthy susceptible piglets at an immunization dose of 2 mL.

Blood Collection after Immunization:

The antibody production after immunization was monitored: on the 7th, 14th, 21st, and 28th days after immunization (dpv), serum from each group of healthy susceptible piglets was separated, and the antibody production and window period after the vaccine immunization were detected by the LPB-ELISA antibody kit of Lanzhou Veterinary Research Institute.

The antibody duration of the immunized pigs was monitored: on the 28, 60, 90, 120, 150, 180 and 210 dpv, blood was collected, and the antibody production after the vaccine immunization was detected by the LPB-ELISA antibody kit of Lanzhou Veterinary Research Institute.

(The antibody was qualified when the LPB-ELISA antibody titer was greater than or equal to 26.)

The antibody pass rate after immunization is shown in Table 1 and Table 2.

Figure 1:
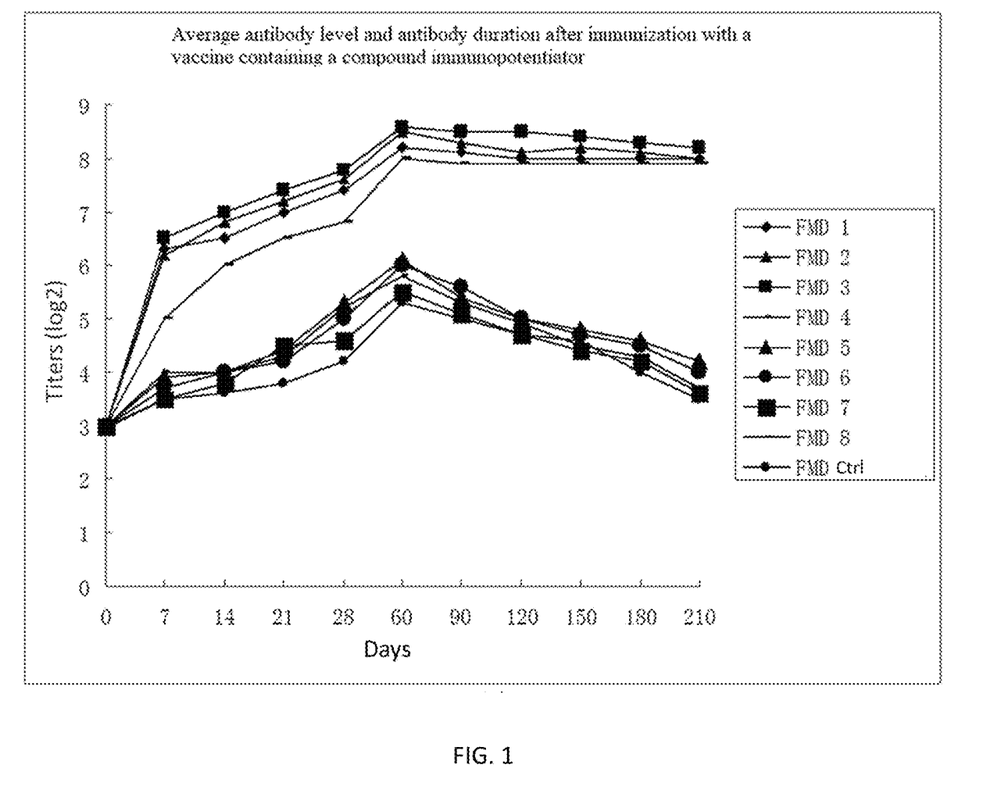
FIG. 1 shows an average antibody level and antibody duration after immunization with a compound immunopotentiator vaccine, and specifically, shows the average liquid-phase blocking ELISA antibody levels of piglets immunized with O-FMD inactivated vaccine containing different compound immunopotentiator components in each group at different time points after immunization.
Figure 2:
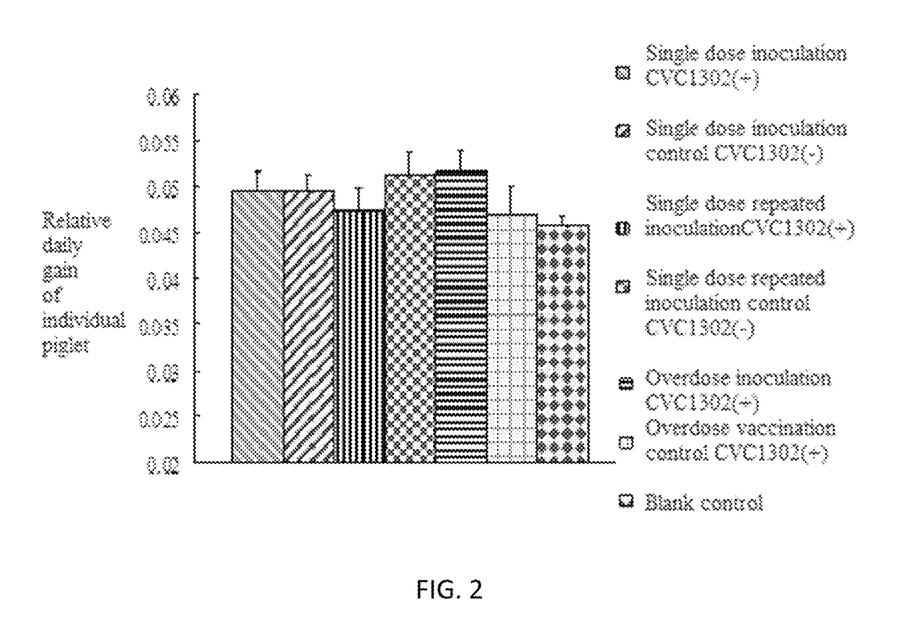
FIG. 2 shows relative daily gain of individual piglet after 28 dpv.
Figure 3:
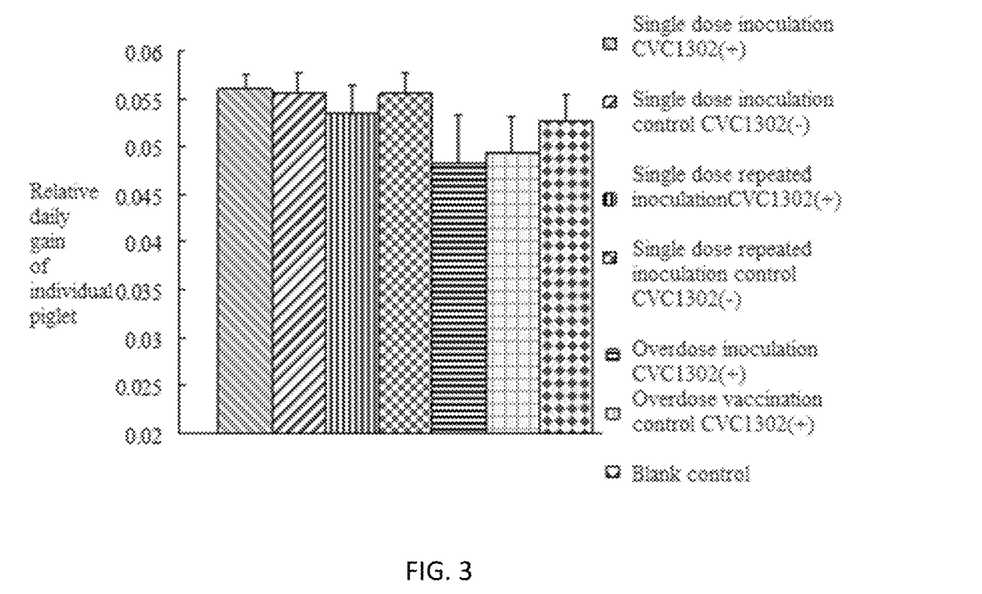
FIG. 3 shows relative daily gain of individual piglet after 56 dpv.
Figure 4A:
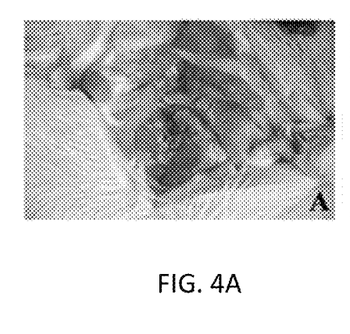
FIG. 4A shows observation of absorption at injection site of piglets after 28 dpv (×400): an experimental group inoculated in a single dose.
Figure 4B:
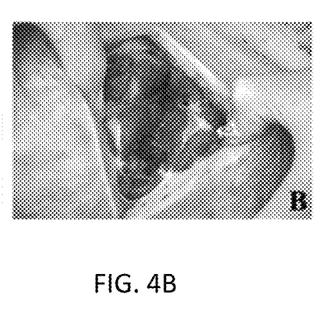
FIG. 4B shows observation of absorption at injection site of piglets after 28 dpv (×400): a control group inoculated in a single dose.
Figure 4C:
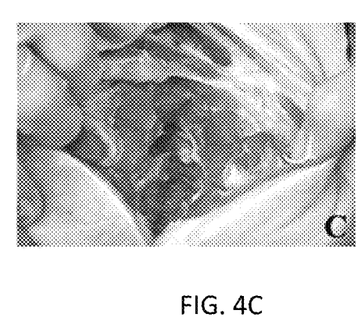
FIG. 4C shows observation of absorption at injection site of piglets after 28 dpv (×400): an experimental group inoculated in an overdose.
Figure 4D:
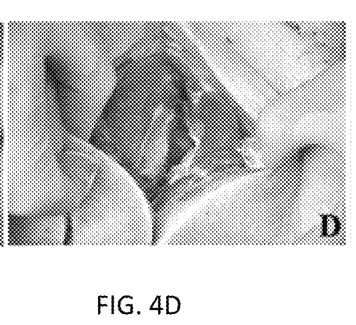
FIG. 4D shows observation of absorption at injection site of piglets after 28 dpv (×400): a control group inoculated in an overdose.
Figure 4E:
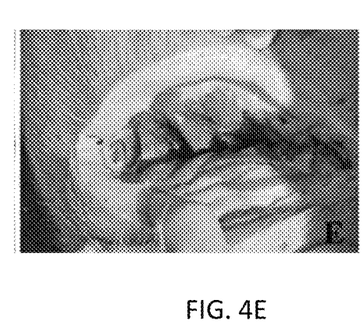
FIG. 4E shows observation of absorption at injection site of piglets after 28 dpv (×400): an experimental group repeatedly inoculated in a single dose
Figure 4F:
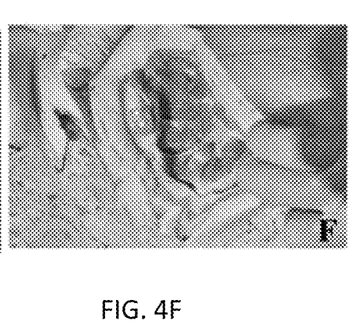
FIG. 4F shows observation of absorption at injection site of piglets after 28 dpv (×400): a control group repeatedly inoculated in a single dose.
Figure 4G:
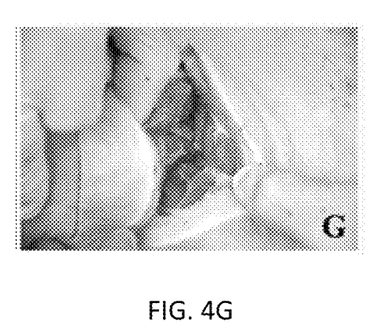
FIG. 4G shows observation of absorption at injection site of piglets after 28 dpv (×400): a blank control group.
Figure 5A:
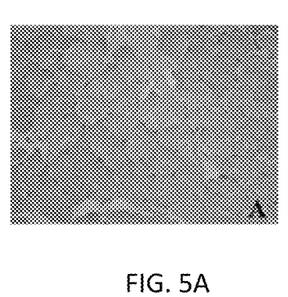
FIG. 5A shows histological observation of neck muscles of piglets after 28 dpv (×400): an experimental group inoculated in a single dose.
Figure 5B:
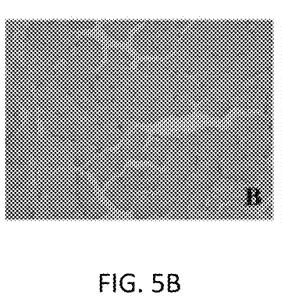
FIG. 5B shows histological observation of neck muscles of piglets after 28 dpv (×400): a control group inoculated in a single dose.
Figure 5C:
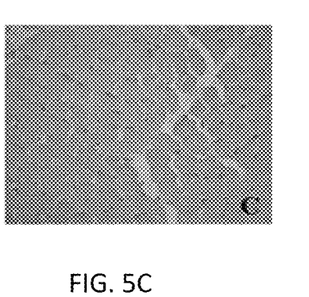
FIG. 5C shows histological observation of neck muscles of piglets after 28 dpv (×400): an experimental group inoculated in an overdose.
Figure 5D:
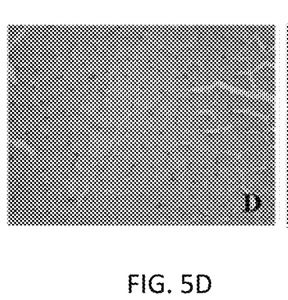
FIG. 5D shows histological observation of neck muscles of piglets after 28 dpv (×400): a control group inoculated in an overdose.
Figure 5E:
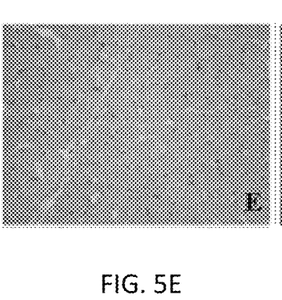
FIG. 5E shows histological observation of neck muscles of piglets after 28 dpv (×400): an experimental group repeatedly inoculated in a single dose.
Figure 5F:
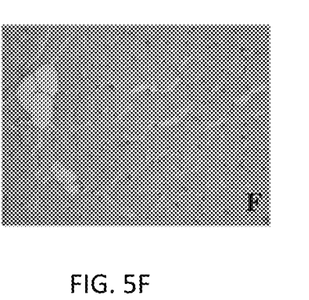
FIG. 5F shows histological observation of neck muscles of piglets after 28 dpv (×400): a control group repeatedly inoculated in a single dose.
Figure 5G:
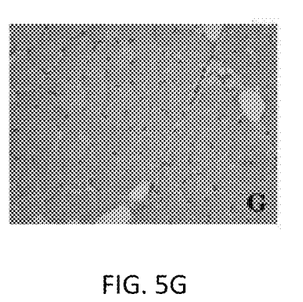
FIG. 5G shows histological observation of neck muscles of piglets after 28 dpv (×400): a blank control group.

The average antibody level after immunization is shown in FIG. 1.

TABLE 1

Antibody pass rate after immunization for each group of piglets

| Tag | Immunization vaccine | 7 dpv | 14 dpv | 21 dpv | 28 dpv |
|---|---|---|---|---|---|
| 1 | FMD 1 | 8/10 | 9/10 | 9/10 | 10/10 |
| 2 | FMD 2 | 8/10 | 9/10 | 10/10 | 10/10 |
| 3 | FMD 3 | 9/10 | 10/10 | 10/10 | 10/10 |
| 4 | FMD 4 | 4/10 | 4/10 | 5/10 | 5/10 |
| 5 | FMD 5 | 4/10 | 4/10 | 5/10 | 5/10 |
| 1-1 | FMD 1-1 | 2/10 | 3/10 | 4/10 | 4/10 |
| 3-1 | FMD 3-1 | 2/10 | 3/10 | 4/10 | 4/10 |
| 6 | FMD 6 | 4/10 | 4/10 | 5/10 | 5/10 |
| 7 | FMD 7 | 2/10 | 2/10 | 3/10 | 3/10 |
| 8 | FMD 8 | 5/10 | 9/10 | 10/10 | 10/10 |
| 9 | FMD control vaccine | 2/10 | 3/10 | 3/10 | 3/10 |

Remarks: in Table 1, 7 dpv, 14 dpv, 21 dpv, and 28 dpv represent 7 days after immunization (dpv), 14 dpv, 21 dpv, 28 dpv respectively; the numbers upper and down the symbol "/" respectively represent: the number of pigs with the antibody reaching the acceptance line/the number of pigs that were immunized.

It can be seen that from Table 1 that in 10 piglets immunized with the FMD control vaccine, only the antibodies of two reached the acceptance line in 7 dpv, and the pass rate was 2/10; the FMD 6 group solely added with *astragalus* polysaccharide as an immunopotentiator had a certain immunopotentiating effect at high dose levels, but the effect was also unsatisfactory, which was significantly worse than that of FMD 1/FMD 2/FMD 3 groups (the pass rates were 8/10, 8/10 and 9/10); the single low-dose *astragalus* polysaccharide group (FMD 7) had poorer immunopotentiating effect; high-dose *astragalus* polysaccharides compounded with different doses of MPL, MDP and β-glucan (FMD 4/FMD 5) have no obvious immunopotentiating effect, but lower-dose *astragalus* polysaccharides compounded with low-dose MPL, MDP, and β-glucan (FMD 1/FMD 2/FMD 3) can apparently shorten the window period of the antibody to 7 days, and more than 80% of the antibodies can reach the acceptance line within 7 days (the liquid phase blocking ELISA antibody was greater than $2^6$) without reducing the pass rate of the antibodies (compared with FMD 8). Formulations of two compositions 1 and 3 were 1-1 and 3-1 respectively without adding the *astragalus* polysaccharide. Compared with the FMD 8 group, doses of the two formulations were reduced, and the immune effect was also significantly reduced (the antibody pass rate after 7 days to 28 days was significantly reduced). After the synergistic effect of the *astragalus* polysaccharide was absent, antibody pass rates of 1-1 and 3-1 groups were significantly lower than those of 1 and 3 groups. In the FMD 8 group, there was also a significant immunopotentiating level, but the window period for antibody production was delayed by seven days than that of FMD 1/FMD 2/FMD 3; the antibody pass rate on the 14 dpv was equivalent to the compound immunopotentiators 1/2/3 (FMD 1/FMD 2/FMD 3); and the antibody pass rate on the 14 dpv was equivalent to the pass rate of the corresponding compound immunopotentiators 1, 2 and 3 (FMD 1/FMD 2/FMD 3) on the 7 dpv.

TABLE 2

Antibody pass rates during antibody duration after immunization for each group of piglets

| Tag | Immunization vaccine | 28 dpv | 60 dpv | 90 dpv | 120 dpv | 150 dpv | 180 dpv | 210 dpv |
|---|---|---|---|---|---|---|---|---|
| 1 | FMD 1 | 10/10 | 10/10 | 10/10 | 10/10 | 10/10 | 10/10 | 10/10 |
| 2 | FMD 2 | 10/10 | 10/10 | 10/10 | 10/10 | 10/10 | 10/10 | 10/10 |
| 3 | FMD 3 | 10/10 | 10/10 | 10/10 | 10/10 | 10/10 | 10/10 | 10/10 |
| 4 | FMD 4 | 5/10 | 5/10 | 4/10 | 4/10 | 3/10 | 3/10 | 3/10 |
| 5 | FMD 5 | 5/10 | 5/10 | 5/10 | 4/10 | 4/10 | 4/10 | 4/10 |
| 1-1 | FMD 1-1 | 4/10 | 4/10 | 4/10 | 3/10 | 3/10 | 3/10 | 3/10 |
| 3-1 | FMD 3-1 | 4/10 | 4/10 | 4/10 | 3/10 | 3/10 | 3/10 | 3/10 |
| 6 | FMD 6 | 5/10 | 5/10 | 5/10 | 4/10 | 4/10 | 3/10 | 3/10 |
| 7 | FMD 7 | 3/10 | 3/10 | 3/10 | 3/10 | 2/10 | 2/10 | 2/10 |
| 8 | FMD 8 | 10/10 | 10/10 | 10/10 | 9/10 | 9/10 | 9/10 | 810 |
| 9 | FMD control vaccine | 3/10 | 3/10 | 3/10 | 2/10 | 2/10 | 2/10 | 2/10 |

It can be seen from Table 2 that the three groups of immunopotentiator formulations 1, 2 and 3, i.e., FMD 1/FMD 2/FMD 3, can significantly prolong the antibody duration of the vaccine after immunization, and the antibody pass rate was observed to have no significant decrease in seven months after the immunization, which was maintained at 10/10; the highest pass rate of the FMD control vaccine was basically at 3/10; the single *astragalus* polysaccharide group (FMD 6/FMD 7) and groups (FMD 1-1 and 3-1 groups) that the *astragalus* polysaccharide in the compound immunopotentiators 1, 2 and 3 was reduced and removed had a certain immunopotentiating effect, but the effect was not obvious, which was not significantly different from the FMD control vaccine.

It can be seen from FIG. 1 that the groups of the compound immunopotentiators 1, 2 and 3 (FMD 1/FMD 2/FMD 3) and the group of the immunopotentiator 8 (FMD 8) can significantly improve the immune effects of the FMD vaccine and shorten the window period for antibody production; wherein the average LPB-ELISA antibody levels of the groups of the compound immunopotentiator 1, 2, and 3 (FMD 1/FMD 2/FMD 3) were higher than $2^6$ on the 7 dpv, which was much higher than that of $2^3$ of the control vaccine group, significantly increasing the average antibody level and antibody duration. The group of the single *astragalus* polysaccharide (FMD 6/FMD 7) and high-dose *astragalus* polysaccharide compounded with the MPL, MDP and β-glucan (FMD 4/FMD 5) and the low-dose MPL, MDP, and β-glucan (FMD 1-1 and 3-1) were significantly lower than the groups of the compound immunopotentiators 1, 2, and 3, and had no obvious immunopotentiating effect compared with a FMD inactivated vaccine group.

Therefore, due to the synergistic effect of the compound immunopotentiator added with a certain amount of *astragalus* polysaccharides and MPL, MDP and β-glucan, the immune response of the piglet to the antigen can be significantly improved, the antibody pass rate and the antibody generation time can be improved, so as to shorten the window period for antibody production of the vaccine to 7 dpv and improve the immune effects of the vaccine.

In this embodiment, the constituents of the compound immunopotentiator can be flexibly matched within a given range, and will not be listed one by one herein.

Third Embodiment: Preparation of Compound Immunopotentiator Partner Vaccine

1. Preparation of Compound Immunopotentiator:

The main ingredients of compound immunopotentiators are: monophosphoryl lipid A, muramyl dipeptide, β-glucan, and *astragalus* polysaccharide. It is prepared by dissolving each main ingredient 0.1 M Tris-HCl with a pH of 8.0.

Compound immunopotentiator 9: the final concentrations of MPL, MDP, β-glucan and *astragalus* polysaccharide were configured to 5.2 μg/mL, 10.4 μg/mL, 1.04 μg/mL and 0.052 mg/mL respectively.

Compound immunopotentiator 10: The final concentrations of MPL, MDP, β-glucan and *astragalus* polysaccharide were configured to 104 μg/mL, 104 μg/mL, 52 μg/mL and 1.04 mg/mL respectively.

Compound immunopotentiator 11: the final concentrations of MPL, MDP, β-glucan and *astragalus* polysaccharide were configured to 520 μg/mL, 520 μg/mL, 520 μg/mL and 5.2 mg/mL respectively.

The prepared compound immunopotentiator was filtered (0.22 μm filter) and sterilized, and then was p sub-packaged in green bottles and stored at 4° C.

2. Preparation of Compound Immunopotentiator Partner Vaccine:

(1) The compound immunopotentiator and Tween were mixed in a volume ratio of 96 to 4, to prepare an aqueous phase.

(2) Marcol 52 mineral oil and Span were thoroughly mixed in a volume ratio of 96 to 4.

(3) The aqueous phase and the oil phase were thoroughly mixed in a volume ratio of 1 to 2, to prepare a partner vaccine containing a relapse immunopotentiator.

The compound immunopotentiator partner vaccines prepared according to this method were respectively named compound immunopotentiator partners 9, 10, and 11 according to the compound immunopotentiators 9, 10 and 11.

3. Method of Application

300 μl partner vaccine containing compound immunopotentiator were thoroughly mixed with the vaccine with a dose for one pig, and then immunization was carried out.

In this embodiment, the constituents of the compound immunopotentiator can be flexibly proportioned within a given range, and the use volume can also be adjusted according to the actual needs, and will not be listed one by one herein.

Fourth Embodiment: Evaluation of Immune Effects of Compound Immunopotentiator Partner Vaccine on Commercially Available FMD O, A and Asia-I Trivalent Vaccines 1. Preparation of Vaccine:

The three partner vaccines prepared in the third embodiment were adopted as the compound immunopotentiator partner vaccines.

The trivalent vaccines are O, A and Asia-I inactivated trivalent vaccines (fine vaccine) with a lot No. of 5235039, 20151224.

2. Grouping, Immunization and Antibody Detection

Experimental grouping and immunization: healthy susceptible piglets were randomly divided into four groups in total with each group having 10 piglets.

Each group of vaccines was immunized with a group of healthy susceptible piglets.

TABLE 3

| Vaccine immunization and grouping | | |
|---|---|---|
| Grouping | Immunization vaccine | Immunized number of pigs |
| 1 | Compound immunopotentiator partner vaccine 9 + trivalent vaccine | 10 |
| 2 | Compound immunopotentiator partner vaccine 10 + trivalent vaccine | 10 |
| 3 | Compound immunopotentiator partner vaccine 11 + trivalent vaccine | 10 |
| 4 | Trivalent vaccine | 10 |

Blood Collection After Immunization:

The antibody production after immunization was monitored: on the 7, 14, 21, and 28 dpv, serum from each group of healthy susceptible piglets was separated, and the antibody production and window period after the vaccine immunization were detected by the LPB-ELISA antibody kit of Lanzhou Veterinary Research Institute.

The antibody duration of the group of the compound immunopotentiator with better immunopotentiating after immunization was monitored: on the 28, 60, 90, 120, 150, 180 and 210 dpv, serum from each group of healthy susceptible piglets was separated, and the antibody production and window period after the vaccine immunization were detected by the LPB-ELISA antibody kit of Lanzhou Veterinary Research Institute.

(The antibody was qualified when the O type LPB-ELISA antibody titer was greater than or equal to $2^6$, and the antibody was qualified when the A type and the Asia-I type LPB-ELISA antibody titer was greater than or equal to $2^7$.)

The antibody pass rate after immunization was shown in Table 4 and Table 5.

TABLE 4

| Antibody pass rate after immunization for each group of piglets | | | | |
|---|---|---|---|---|
| Tag | Immunization vaccine | 7 dpv O/A/Asia-I (qualified number of pigs) | 14 dpv O/A/Asia-I (qualified number of pigs) | 21 dpv O/A/Asia-I (qualified number of pigs) |
| 1 | Compound immunopotentiator partner vaccine 9 + trivalent vaccine | 7/8/5 | 8/9/5 | 9/9/6 |
| 2 | Compound immunopotentiator partner vaccine 10 + trivalent vaccine | 7/8/5 | 8/8/6 | 8/9/6 |
| 3 | Compound immunopotentiator partner vaccine 11 + trivalent vaccine | 8/9/6 | 9/9/7 | 9/9/7 |
| 4 | Trivalent vaccine | 2/3/1 | 3/4/2 | 5/4/2 |

It can be seen that from Table 4 that the antibody pass rates of three serotypes of the piglets immunized with the trivalent vaccine were only 20%, 30% and 10% in 7 dpv; while the antibody pass rates of the piglets immunized with the compound immunopotentiator partner vaccine 9/10/11+ the trivalent vaccine can reach 70 to 90% in 7 dpv, and the window period was shortened obviously; and the LPB-ELISA antibody pass rate was also increased significantly.

TABLE 5

| Antibody pass rates during antibody duration after immunization for each group of piglets | | | | | | | | |
|---|---|---|---|---|---|---|---|---|
| Tag | Immunization vaccine | 28 dpv | 60 dpv | 90 dpv | 120 dpv | 150 dpv | 180 dpv | 210 dpv |
| 1 | Compound immunopotentiator partner vaccine 9 + trivalent vaccine | 9/9/6 | 9/9/6 | 9/9/6 | 9/9/6 | 9/9/6 | 9/9/6 | 9/9/6 |
| 2 | Compound immunopotentiator partner vaccine 10 + trivalent vaccine | 8/9/7 | 8/9/7 | 9/9/7 | 9/9/7 | 8/9/7 | 8/9/7 | 8/9/7 |
| 3 | Compound immunopotentiator partner vaccine 11 + trivalent vaccine | 9/9/7 | 9/98 | 9/9/8 | 9/9/8 | 9/9/8 | 9/9/8 | 9/9/7 |
| 4 | Trivalent vaccine | 5/4/2 | 5/4/2 | 4/4/2 | 4/4/2 | 4/3/2 | 4/3/2 | 3/3/2 |

It can be seen from Table 5 that the antibodies of piglets immunized with the trivalent vaccine were slowly declined from the 90 dpv; while the antibody levels of piglets immunized with the compound immunopotentiator partner vaccine 9/10/11+ trivalent vaccine were substantially stable on the 28 dpv, and had no apparent declining trend to seven months; The immunization group added with the compound immunopotentiator partner vaccine significantly extended the antibody duration of the vaccine.

In summary, the compound immunopotentiator partner vaccine has significantly improved the immune effects of the O, A and Asia-I trivalent foot-and-mouth disease inactivated vaccine, has apparent immunopotentiating effects on the antibodies of the three O, A and Asia-I serotypes, and significantly shortens the window period for antibody production, and improves the antibody duration of the vaccine.

Fifth Embodiment: Evaluation of Immune Effects of Compound Immunopotentiator Partner Vaccine on Commercially Available Polypeptide Vaccines 1. Preparation of Vaccine:

The three partner vaccines prepared in the third embodiment were adopted as the compound immunopotentiator partner vaccines.

Polypeptide vaccine lot number: (2014) 090297522

2. Grouping, Immunization and Antibody Detection

Experimental grouping and immunization: healthy susceptible piglets were randomly divided into four groups in total with each group having 10 piglets.

Each group of vaccines was immunized with a group of healthy susceptible piglets.

TABLE 6

Vaccine immunization and grouping

| Grouping | Immunization vaccine | Immunized number of pigs |
|---|---|---|
| 1 | Compound immunopotentiator partner vaccine 9 + polypeptide vaccine | 10 |
| 2 | Compound immunopotentiator partner vaccine 10 + polypeptide vaccine | 10 |
| 3 | Compound immunopotentiator partner vaccine 11 + polypeptide vaccine | 10 |
| 4 | Polypeptide vaccine | 10 |

Blood Collection After Immunization:

The antibody production after immunization was monitored: on the 7, 14, 21, and 28 dpv, blood serum was collected from healthy susceptibility piglets in each group. The liquid-phase-interacting ELISA antibody detection kit of Lanzhou Veterinary Research Institute and foot-and-mouth disease virus VP1 structural protein antibody ELISA diagnostics kit (polypeptide antibody kit purchased from Shanghai Shen Lian Biomedical Corporation) were used to detect antibody production after immunization with the vaccine respectively.

The antibody duration of the group of the compound immunopotentiator with better immunopotentiating after immunization was monitored: on the 28, 60, 90, 120, 150, 180 and 210 dpv, blood was collected, and the serum antibody production after the vaccine immunization was detected by the LPB-ELISA antibody kit of Lanzhou Veterinary Research Institute.

(The antibody was qualified when the LPB-ELISA antibody titer was greater than or equal to $2^6$, and a kit determination criteria was used to determine the polypeptide antibody test uses the kit criteria for positive and negative determination during the polypeptide antibody detection.)

The antibody pass rates detected by the two kits after immunization were shown in Table 7 and Table 8.

TABLE 7

Antibody pass rate after immunization for each group of piglets

| | Immunization | (Number of pigs with qualified liquid-phase ELISA/number of pigs with qualified polypeptide antibody) | | |
|---|---|---|---|---|
| Tag | vaccine | 7 dpv | 14 dpv | 21 dpv |
| 1 | Compound immunopotentiator Partner vaccine 9 + polypeptide vaccine | 5/8 | 6/9 | 6/10 |
| 2 | Compound immunopotentiator Partner vaccine 10 + polypeptide vaccine | 5/8 | 6/9 | 6/10 |
| 3 | Compound immunopotentiator partner vaccine 11 + polypeptide vaccine | 6/9 | 7/10 | 7/10 |
| 4 | Commercially available vaccine | 0/4 | 0/5 | 1/7 |

It can be seen that from Table 7 that the polypeptide antibody pass rate of piglets immunized with the polypeptide vaccine was 4/10 in 7 dpv; but the LPB-ELISA antibody pass rate was O; while the polypeptide antibody pass rate of piglets immunized with the compound immunopotentiator partner vaccine 9/10/11+ polypeptide vaccine was 8/10 or 9/10 in 7 dpv; and the LPB-ELISA antibody pass rate could also be improved to 5/10 or 6/10 about. It was found in the LPB-ELISA antibody kit of Lanzhou Veterinary Research Institute that the LPB-ELISA antibody level had a certain correlation with protective efficiency. In particular, the higher the antibody level was, the better the protection effect was. The compound immunopotentiator partner vaccine can significantly shorten the window period for antibody production of the polypeptide vaccine, and increase the pass rate of the LPB-ELISA antibody.

TABLE 8

Antibody pass rates during antibody duration after immunization for each group of piglets

| | | (Number of pigs with qualified liquid-phase ELISA/number of pigs with qualified polypeptide antibody) | | | | | | |
|---|---|---|---|---|---|---|---|---|
| Tag | Vaccine | 28 dpv | 60 dpv | 90 dpv | 120 dpv | 150 dpv | 180 dpv | 210 dpv |
| 1 | Compound immunopotentiator partner vaccine 9 + polypeptide vaccine | 6/10 | 7/10 | 7/10 | 6/10 | 6/10 | 6/9 | 6/9 |
| 2 | Compound immunopotentiator partner vaccine 10 + polypeptide vaccine | 6/10 | 7/10 | 7/10 | 7/10 | 7/10 | 6/10 | 6/10 |

TABLE 8-continued

Antibody pass rates during antibody duration after immunization for each group of piglets

| | | (Number of pigs with qualified liquid-phase ELISA/number of pigs with qualified polypeptide antibody) | | | | | | |
|---|---|---|---|---|---|---|---|---|
| Tag | Vaccine | 28 dpv | 60 dpv | 90 dpv | 120 dpv | 150 dpv | 180 dpv | 210 dpv |
| 3 | Compound immunopotentiator partner vaccine 11 + polypeptide vaccine | 7/10 | 7/10 | 7/10 | 7/10 | 7/10 | 7/10 | 7/10 |
| 4 | Polypeptide vaccine | 1/7 | 1/7 | 0/5 | 0/5 | 0/5 | 0/5 | 0/5 |

It can be seen from Table 8 that the antibodies of piglets immunized with the polypeptide vaccine were slowly declined from the 90 dpv; while the antibody levels of piglets immunized with the compound immunopotentiator partner vaccine 9/10/11+ polypeptide vaccine were substantially stable on the 21 dpv, and had no apparent declining trend to seven months. The immunization group added with the compound immunopotentiator partner vaccine significantly extended the antibody duration of the vaccine.

In summary, the compound immunopotentiator partner vaccine can significantly improve the immune effects of the foot-and-mouth disease polypeptide vaccine, and can obviously improve the pass rate of the LPB-ELISA antibody, and obviously shorten the window period for antibody production of the vaccine and increase the antibody duration of the vaccine.

Sixth Embodiment: Safety Evaluation of Compound Immunopotentiator on Piglets 1. Configuration of Immunopotentiator Main components of the immunopotentiator were: monophosphoryl lipid A (MPL), muramyl dipeptide (MDP), β-glucan and *astragalus* polysaccharide. A preparation method thereof was to dissolve the main components in 0.1 M Tris-HCl of a pH 8.0. A safety of the compound immunopotentiator was evaluated. A compound immunopotentiator 11 with a highest dose was selected (final concentrations of MPL, MDP, β-glucan and *astragalus* polysaccharide were configured to 520 μg/mL, 520 μg/mL, 520 μg/mL and 5.2 mg/mL respectively).

2. Grouping, Immunization and Observation

Experimental grouping and immunization: healthy susceptible piglets were randomly divided into seven groups with each group having five piglets. The immunopotentiator was mixed with a commercial porcine FMD O type vaccine in a form of companion before immunization for immunization. According to requirements for a vaccine safety evaluation test in the No. 442 Announcement, 40-day-old healthy piglets were randomly divided into seven groups with each group having six piglets, comprising: an experimental group inoculated with a CVC1302 adjuvant (+) in a single dose and a control group inoculated with a CVC1302 adjuvant (−) in a single dose; an experimental group repeatedly inoculated with the CVC1302 adjuvant (+) in a single dose and a control group repeatedly inoculated with the CVC1302 adjuvant (−) in a single dose; an experimental group inoculated with the CVC1302 adjuvant (+) in an overdose (two times dose), a control group inoculated with the CVC1302 adjuvant (−) in an overdose (two times dose), and a blank control group.

Immunization of piglets: intramuscular injection in neck, and repeated inoculation in a single dose at an interval of two weeks.

After immunization, whether the experimental piglets had local reactions of red swelling, induration, itching, lymphadenopathy and other symptoms at an injection site, and whether the experimental piglets had diarrhea, rash, edema, purpura, irritability, loss of appetite, vomiting and other general symptoms were observed.

After each immunization, clinical changes of all experimental piglets were carefully observed, comprising a body temperature, feeding, a mental state, local stimulation, etc., for 7 consecutive days. All piglets were weighed on a day of immunization, and were weighed after the 28 dpv and the 56 dpv respectively to calculate a relative daily gain of an individual. Relative daily gain of individual=(weight after inoculation−weight on day of inoculation)/days/weight on day of inoculation. After the 28 dpv and the 56 dpv, three piglets in each group were dissected for routine pathological clinical examination, focusing on examination of immune system-related tissues and organs comprising thymus, spleen, submandibular lymph nodes, mesenteric lymph nodes, axillary lymph nodes, inguinal lymph nodes, etc., and histological observation was performed if obvious pathological organs were observed. Muscular tissues of an inoculation site were taken for the histological observation. In addition, a heart, a liver, a spleen, a kidney and a lung were weighed respectively to calculate organ coefficients. Organ coefficient=(ratio of organ weight to body weight)×100.

3. Results 3.1 Clinical Observation Results After Immunization Were Shown in the Following Table:

TABLE 9

Side effects of experimental piglets after vaccine immunization

| Grouping | Potentiator | Side effects after immunization |
|---|---|---|
| G1 | 1x | 6 hours after immunization, the experimental piglets were anorectic and prone to lying, without an obvious change in a body temperature; 12 hours after immunization, feeding began to recover obviously; 24 hours after immunization, the feeding was completely normal; until 14 days after immunization, no enlargement of lymph nodes was found at the injection site. |
| G2 | 3x | 6 hours after immunization, the experimental piglets were anorectic and prone to lying, without an obvious change in a body temperature; |

TABLE 9-continued

Side effects of experimental piglets after vaccine immunization

| Grouping | Potentiator | Side effects after immunization |
|---|---|---|
| | | 12 hours after immunization, feeding began to recover obviously; 24 hours after immunization, the feeding was completely normal; d until 14 days after immunization, no enlargement of lymph nodes was found at the injection site. |
| G3 | 5x | 6 hours after immunization, the experimental piglets were anorectic and prone to lying, without an obvious change in a body temperature; 12 hours after immunization, feeding began to recover; 24 hours after immunization, the feeding was basically normal; until 14 days after immunization, no enlargement of lymph nodes was found at the injection site. |
| G4 | Control | 6 hours after immunization, the experimental piglets are occasionally anorectic and prone to lying, without an obvious change in a body temperature; 12 hours after immunization, began is recovered; 24 hours after immunization, the feeding became normal; and until 14 days after immunization, no enlargement of lymph nodes was found at the injection site. |

Addition of the immunopotentiator 3 in each dose could cause a slight stress reaction of the piglets upon observation, but the piglets were basically normal within 12 hours, without a clinical manifestation or a weight effect.

3.2 Effect of Foot-and-Mouth Disease Vaccine Compounded with CVC1302 on Growth Performance of Piglets The piglets immunized with the foot-and-mouth disease vaccine compounded with CVC1302 had no statistic difference in the relative daily gain of piglets among the experimental groups after the 28 dpv and the 56 dpv.

3.3 Absorption of Foot-and-Mouth Disease Vaccine Compounded with CVC1302 at Injection Site The piglets were dissected after the 28 dpv, and the vaccine was well absorbed in neck muscles by visual observation, without vaccine residue, and no significant difference was found between each experimental group and the blank control group (FIG. 4). Histological observation of the neck muscles showed that: muscle fibers were arranged neatly, no proliferation of inflammatory cells and granulation tissues was found among muscle bundles, and the neck muscles were all normal among the experimental groups (FIG. 5).

The piglets were dissected after the 56 dpv, and the vaccine was well absorbed in neck muscles in each experimental group by visual observation (results were not shown). The neck muscles were all normal among the experimental groups by the histological observation (results were not shown).

To sum up, the compound immunopotentiator added as a vaccine was safe for the piglets, without obvious clinical changes and abnormal changes at a vaccination site. The tested piglets had a good growth performance. The vaccine could be completely absorbed after the 28 dpv.

The descriptions above are only the preferable embodiments of the present invention, and it should be noted that those of ordinary skills in the art may make a plurality of improvements and decorations without departing from the principle of the present invention, and these improvements and decorations shall also fall within the protection scope of the present invention.

What is claimed is:

1. An adjuvant composition comprises the following:
    a) 5 to 520 µg/mL monophosphoryl lipid,
    b) 10 to 520 µg/mL muramyl dipeptide,
    c) 1 to 520 µg/mL β-glucan, and
    d) 0.05 to 5.2 mg/mL *astragalus* polysaccharide; wherein the *astragalus* polysaccharide is prepared by the following steps: i) soaking *Astragalus membranaceus* in an equal amount of distilled water by weight for 2 to 12 hours, boiling for one hour, and collecting supernatant and precipitates separately; ii) adding additional equal amount of distilled water to the precipitates, boiling one hour, collecting supernatant, and repeat step ii); iii) combining three supernatants, filter to yield filtrate, and concentrate the filtrate to about 1 gram/ml of crude polysaccharide; and iv) precipitating the crude polysaccharide with 60% and 80% ethanol to yield polysaccharide precipitates, adding distilled water to the polysaccharide precipitates, and drying to yield the *astragalus* polysaccharide.

2. The adjuvant composition according to claim 1, wherein the adjuvant composition comprises the following:
    a) 5 to 500 µg/mL monophosphoryl lipid,
    b) 10 to 500 µg/mL muramyl dipeptide,
    c) 1 to 500 µg/mL β-glucan, and
    d) 0.05 to 5.0 mg/mL *astragalus* polysaccharide.

3. The adjuvant composition according to claim 2, wherein the adjuvant composition comprises the following:
    a) 100 to 500 µg/mL monophosphoryl lipid,
    b) 100 to 500 µg/mL muramyl dipeptide,
    c) 50 to 500 µg/mL β-glucan, and
    d) 1 to 5.0 mg/mL *astragalus* polysaccharide.

4. A method of preparing the adjuvant composition according to claim 1, comprising the following steps:
    1) preparing *astragalus* polysaccharide from *Astragalus membranaceus* by the following steps: i) soaking *Astragalus membranaceus* in an equal amount of distilled water by weight for 2 to 12 hours, boiling for one hour, and collecting supernatant and precipitates separately; ii) adding additional equal amount of distilled water to the precipitates, boiling one hour, collecting supernatant, and repeat step ii); iii) combining three supernatants, filter to yield filtrate, and concentrate the filtrate to about 1 gram/ml of crude polysaccharide; and iv) precipitating the crude polysaccharide with 60% and 80% ethanol to yield polysaccharide precipitates, adding distilled water to the polysaccharide precipitates, and drying to yield the *astragalus* polysaccharide;

2) preparing a solution containing monophosphoryl lipid A, muramyl dipeptide, β-glucan and *astragalus* polysaccharide, and mixing the solution with polysorbate 80 to obtain an aqueous phase;
3) mixing mineral oil and sorbitan oleate to obtain an oil solution; and
4) mixing and emulsifying the aqueous phase and the oil solution to obtain the final adjuvant composition.

5. A method of using the adjuvant composition of claim 1, wherein the method comprises administering an effective amount of the adjuvant composition with a vaccine to a subject, wherein the subject is a pig, the vaccine is an inactivated foot-and-mouth disease virus antigen.

6. The method, according to claim 5, wherein the ratio of the inactivated foot-and-mouth disease virus antigen to the adjuvant composition is between 9:1 to 8:1 (V/V).

7. The method according to claim 6, wherein the inactivated foot-and-mouth disease virus antigen from the foot-and-mouth disease virus is derived from one or more of the following strains: O, A and/or Asia-I.

8. The method according to claim 5, wherein the preparation of foot-and-mouth disease virus inactivated vaccine comprising the following steps:
1) mixing the adjuvant composition with at least one inactivated foot-and-mouth disease virus antigen, and then thoroughly mixing the composition with polysorbate 80 to obtain an aqueous phase;
2) mixing mineral oil and sorbitan oleate to obtain an oil solution; and
3)

mixing the aqueous phase of step 1) with the oil solution of step 2), thus obtaining a composition comprising foot-and-mouth disease virus inactivated antigen and the adjuvant composition of claim 1.

* * * * *